(12) United States Patent
Carnevale

(10) Patent No.: US 10,307,567 B2
(45) Date of Patent: Jun. 4, 2019

(54) CATHETER AND METHODS RELATED THERETO

(71) Applicant: Francisco Cesar Carnevale, Sao Paulo (BR)

(72) Inventor: Francisco Cesar Carnevale, Sao Paulo (BR)

( * ) Notice: Subject to any disclaimer, the term of this patent is extended or adjusted under 35 U.S.C. 154(b) by 178 days.

(21) Appl. No.: 14/301,578

(22) Filed: Jun. 11, 2014

(65) Prior Publication Data

US 2014/0371719 A1    Dec. 18, 2014

Related U.S. Application Data

(60) Provisional application No. 61/834,320, filed on Jun. 12, 2013.

(51) Int. Cl.
*A61M 25/00* (2006.01)

(52) U.S. Cl.
CPC ...... *A61M 25/0041* (2013.01); *A61M 25/001* (2013.01); *A61M 2210/12* (2013.01); *A61M 2210/1433* (2013.01); *A61M 2210/166* (2013.01)

(58) Field of Classification Search
CPC .................. A61M 25/001; A61M 25/0041
See application file for complete search history.

(56) References Cited

U.S. PATENT DOCUMENTS

| | | | | |
|---|---|---|---|---|
| 4,822,345 A * | 4/1989 | Danforth | ........... | A61M 25/0054 604/524 |
| 4,961,731 A * | 10/1990 | Bodicky | ............. | A61M 25/007 604/264 |
| 4,964,409 A * | 10/1990 | Tremulis | ............... | A61B 5/0215 600/434 |
| 5,231,994 A * | 8/1993 | Harmjanz | ............. | A61M 25/01 600/434 |
| 5,246,007 A * | 9/1993 | Frisbie | ..................... | A61B 8/12 600/465 |
| 5,295,493 A * | 3/1994 | Radisch, Jr. | ........ | A61B 17/3207 600/585 |
| 5,299,574 A * | 4/1994 | Bower | .............. | A61M 25/0041 600/435 |
| 5,306,263 A * | 4/1994 | Voda | .................. | A61M 25/0041 600/435 |

(Continued)

FOREIGN PATENT DOCUMENTS

WO    WO1996/038196    12/1996
WO    WO2012/130878    10/2012

OTHER PUBLICATIONS

Osiev, Alexander. RU2012145031—Foreign Priority Document for PCT/RU2013/000939 . Oct. 23, 2012. Rupto.*

(Continued)

*Primary Examiner* — William R Carpenter
(74) *Attorney, Agent, or Firm* — Stoel Rives LLP

(57) ABSTRACT

Catheters are disclosed that are configured for insertion into the vasculature connected to the prostate gland of a male patient or uterus of a female patient. Such catheters may comprise a conduit having one or more bends. Conduits with a general U-shaped bend and a compound curve are within the scope of this disclosure Methods related to the catheters, including methods of use and methods of manufacture, are also disclosed.

13 Claims, 11 Drawing Sheets

(56) References Cited

U.S. PATENT DOCUMENTS

| | | | | |
|---|---|---|---|---|
| 5,322,509 | A * | 6/1994 | Rickerd | A61M 25/0041 600/435 |
| 5,401,258 | A * | 3/1995 | Voda | A61M 25/0041 604/523 |
| 5,476,453 | A * | 12/1995 | Mehta | A61M 25/0041 600/435 |
| 5,658,263 | A * | 8/1997 | Dang | A61M 25/0041 604/264 |
| 5,957,911 | A * | 9/1999 | Nesto | A61M 25/0041 600/435 |
| 7,901,425 | B2 * | 3/2011 | Petrick | A61M 25/10 604/528 |
| 2002/0049412 | A1 * | 4/2002 | Madrid | A61F 2/90 604/164.05 |
| 2003/0144657 | A1 * | 7/2003 | Bowe | A61M 25/0041 606/41 |
| 2005/0010237 | A1 * | 1/2005 | Niazi | A61B 17/3415 606/129 |
| 2005/0113801 | A1 * | 5/2005 | Gandras | A61M 25/0041 604/523 |
| 2006/0074308 | A1 | 4/2006 | Rafiee et al. | |
| 2006/0229589 | A1 * | 10/2006 | Itou | A61M 25/0041 604/526 |
| 2007/0149927 | A1 * | 6/2007 | Itou | A61M 25/0041 604/158 |
| 2009/0248034 | A1 * | 10/2009 | Dolan | A61F 2/95 606/128 |
| 2009/0275918 | A1 * | 11/2009 | Crocker | A61M 25/0041 604/508 |
| 2010/0185172 | A1 * | 7/2010 | Fabro | A61B 1/00078 604/500 |
| 2011/0092816 | A1 * | 4/2011 | Bettinotti | A61M 25/0041 600/433 |
| 2011/0112514 | A1 | 5/2011 | McFerran et al. | |
| 2011/0313402 | A1 * | 12/2011 | Morero | A61M 25/0041 604/528 |
| 2012/0029478 | A1 | 2/2012 | Kurasawa et al. | |
| 2014/0088566 | A1 * | 3/2014 | Dangoisse | A61M 25/0041 604/532 |
| 2014/0180323 | A1 * | 6/2014 | Shriver | A61M 25/09025 606/185 |
| 2015/0273136 | A1 * | 10/2015 | Osiev | A61M 25/0041 600/435 |

OTHER PUBLICATIONS

Osiev, Alexander. RU2012145031—Foreign Priority Document for PCT/RU2013/000939 <<Translation>> . Oct. 23, 2012. Rupto.*
International Search Report and Written Opinion dated Oct. 3, 2014 for PCT/BR2014/00201.

* cited by examiner

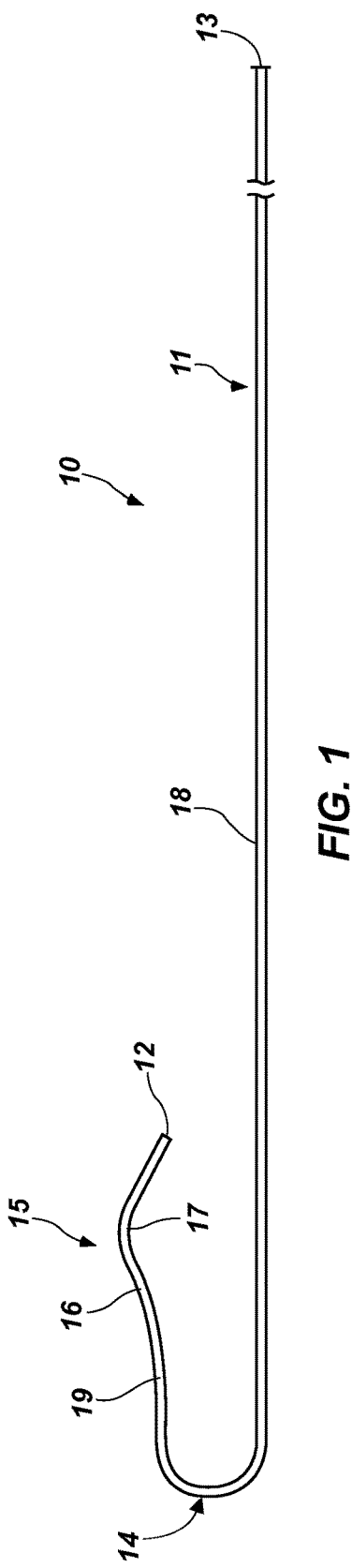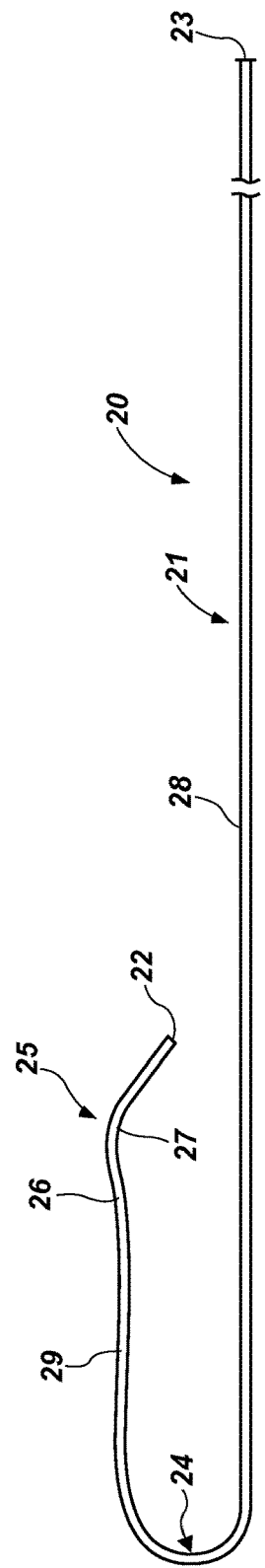

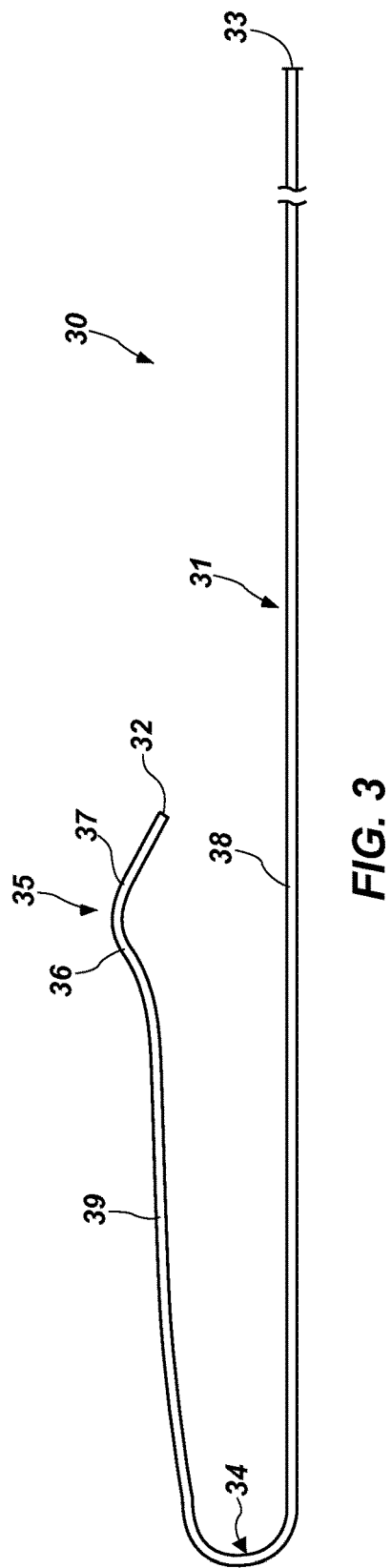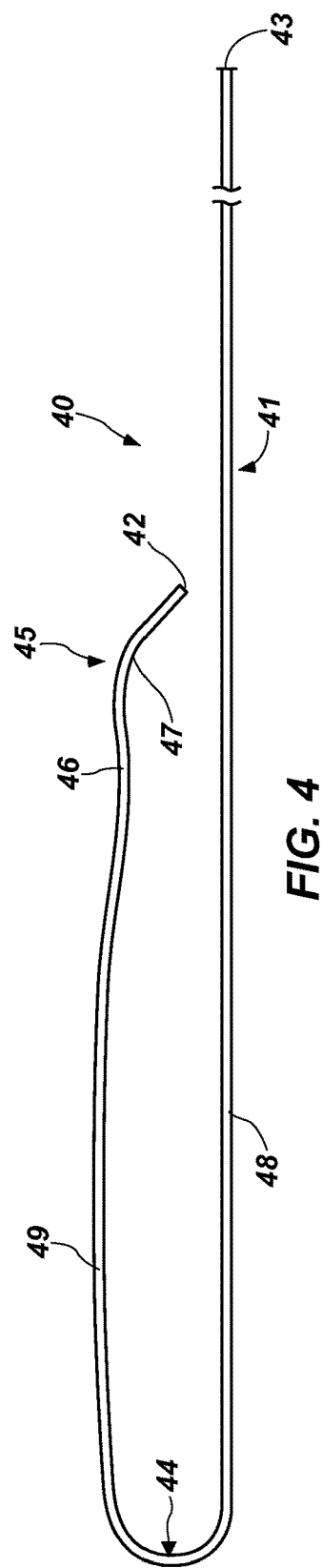

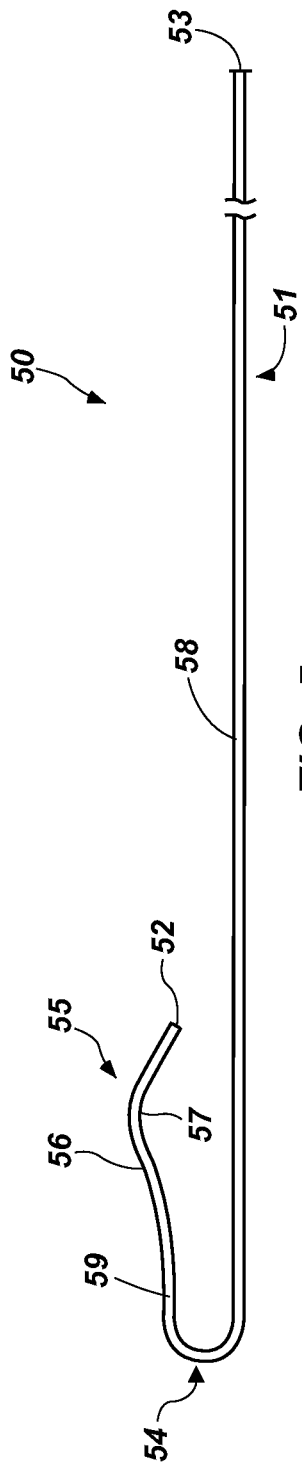
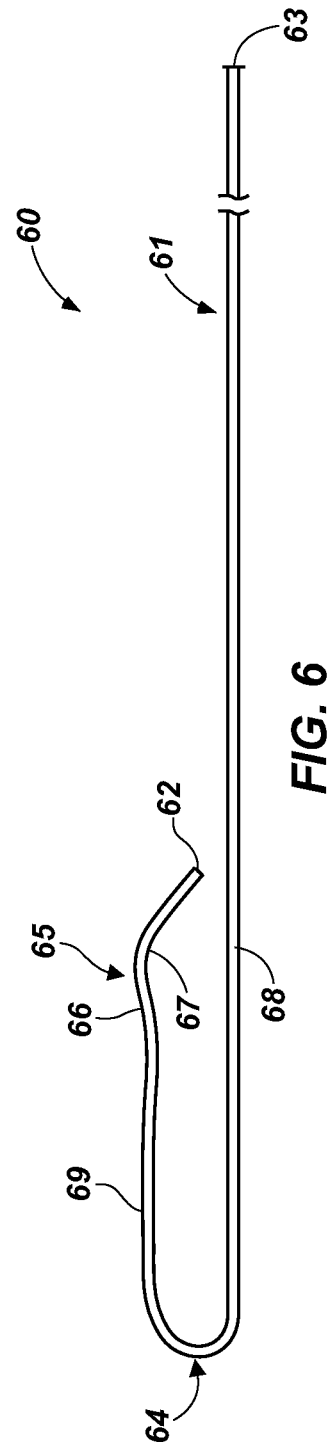
FIG. 5
FIG. 6

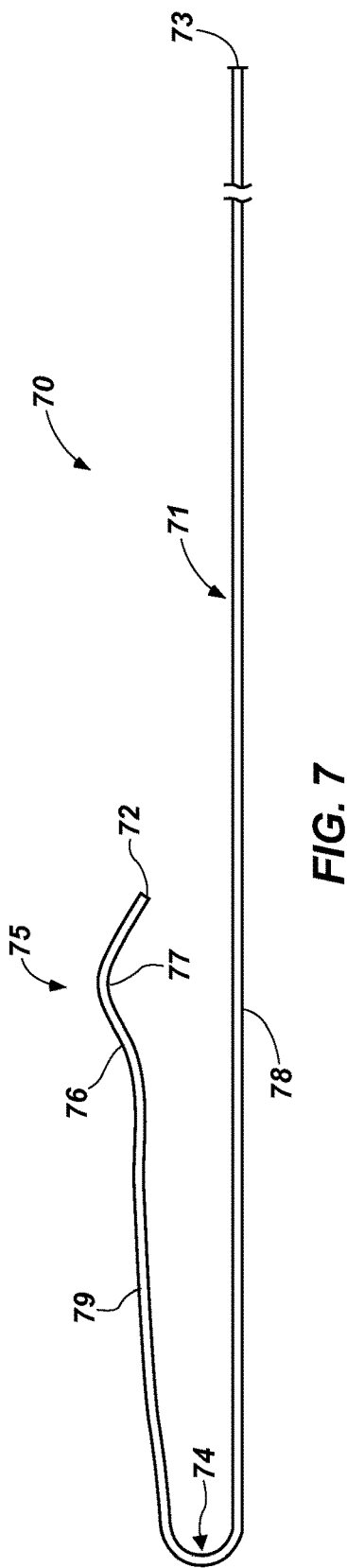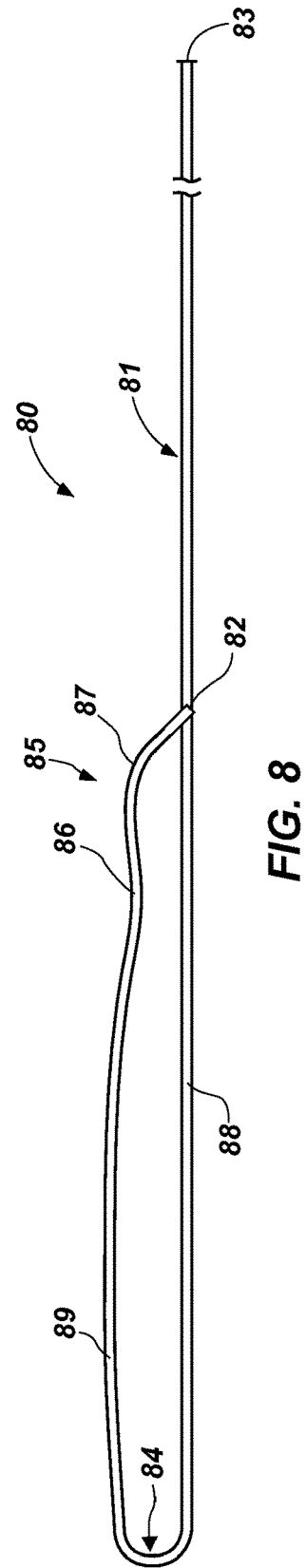

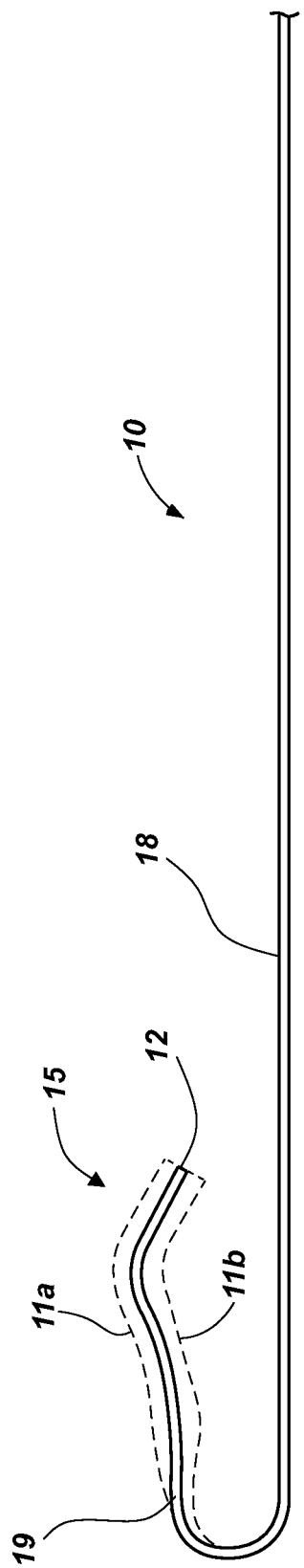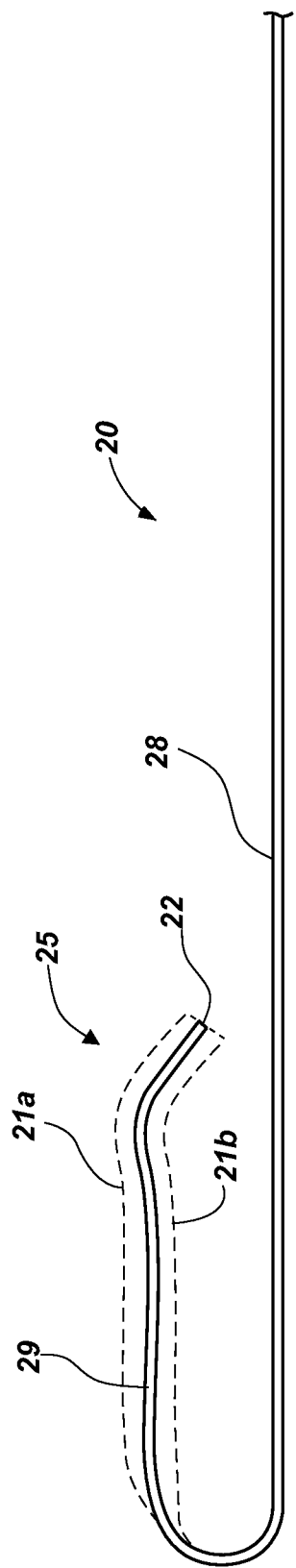

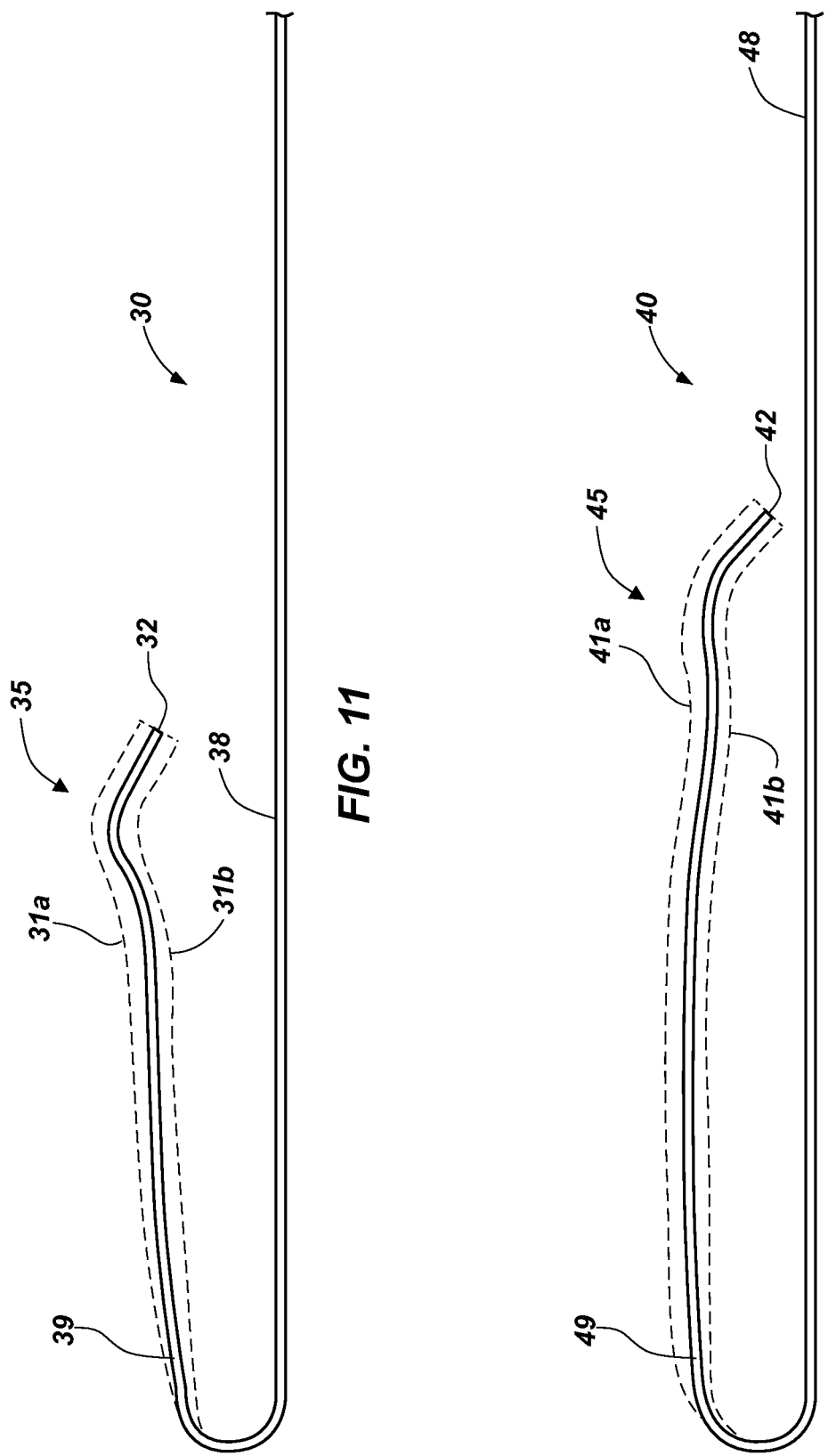

CATHETER AND METHODS RELATED THERETO

RELATED APPLICATIONS

This application claims priority to U.S. Provisional Application No. 61/834,320, filed on Jun. 12, 2013 and titled, "Catheter and Methods Relating Thereto" which is hereby incorporated by reference in its entirety.

TECHNICAL FIELD

The present disclosure relates generally to medical devices. More specifically, the present disclosure relates to catheters. Even more specifically, the present disclosure relates to catheters configured for insertion into the vasculature connected to the prostate gland of a male patient or uterus of a female patient, and methods related thereto.

BRIEF DESCRIPTION OF THE DRAWINGS

The embodiments disclosed herein will become more fully apparent from the following description and appended claims, taken in conjunction with the accompanying drawings. While various aspects of the embodiments are presented in drawings, the drawings are not necessarily drawn to scale unless specifically indicated. These drawings depict only typical embodiments, which will be described with additional specificity and detail through use of the accompanying drawings in which:

FIG. 1 is a side view of one embodiment of a catheter.

FIG. 2 is a side view of another embodiment of a catheter.

FIG. 3 is a side view of yet another embodiment of a catheter.

FIG. 4 is a side view of still another embodiment of a catheter.

FIG. 5 is a side view of an additional embodiment of a catheter.

FIG. 6 is a side view of another additional embodiment of a catheter.

FIG. 7 is a side view of yet another additional embodiment of a catheter.

FIG. 8 is a side view of still another additional embodiment of a catheter.

FIG. 9 illustrates one embodiment of potential variations in the embodiment illustrated in FIG. 1.

FIG. 10 illustrates one embodiment of potential variations in the embodiment illustrated in FIG. 2.

FIG. 11 illustrates one embodiment of potential variations in the embodiment illustrated in FIG. 3.

FIG. 12 illustrates one embodiment of potential variations in the embodiment illustrated in FIG. 4.

DETAILED DESCRIPTION

Figure 13:
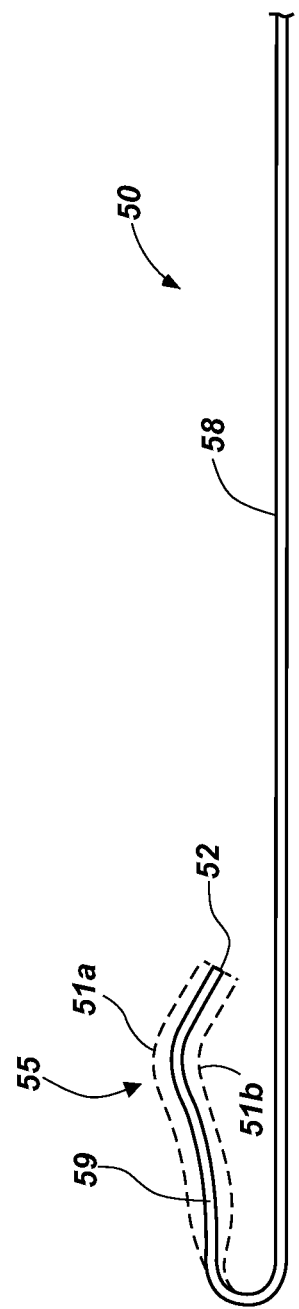
FIG. 13 illustrates one embodiment of potential variations in the embodiment illustrated in FIG. 5.

It will be readily understood that the components of the embodiments as generally described and illustrated in the Figures herein could be arranged and designed in a wide variety of different configurations. Thus, the following more detailed description of various embodiments, as represented in the Figures, is not intended to limit the scope of the disclosure, but is merely representative of various embodiments.

Medical apparatuses may be deployed in various body lumens for a variety of purposes. For example, for the treatment Benign Prostate Hyperplasia (BPH) and/or prostate cancer, it may be desirable to insert a microcatheter into the blood vessels that supply the prostate gland. Embolic materials may then be delivered through the microcatheter into the blood vessels to block the supply of blood to the prostate gland. Likewise, for the treatment of uterine fibroids and/or adenomyosis, embolic materials may be delivered through the microcatheter to block the blood vessels that supply blood to the uterus. Guidewires may be deployed, for example, throughout the vascular system to guide the placement or removal of catheters and other medical apparatuses. At times it is desired to use a catheter, termed a "delivery catheter," to guide placement of a microcatheter that slides inside the lumen of the catheter. The microcatheter is then used to deliver the embolic materials.

The phrase "connected to" refers to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The directional terms "proximal" and "distal" are used herein to refer to opposite locations. For example, the proximal end of a catheter is defined as the end closest to the user during insertion or utilization of the catheter. The distal end is the end opposite the proximal end, along the longitudinal direction of the catheter.

FIG. 1 illustrates one embodiment of a catheter 10. Catheter 10 comprises a conduit 11. The conduit 11 may comprise a single lumen. The conduit 11 comprises a distal end 12 configured for vascular insertion and a proximal end 13. The conduit 11 comprises a general U-shaped bend 14 near the distal end 12. The conduit 11 further comprises a compound curve 15 between the distal end 12 and the general U-shaped bend 14. The compound curve 15 comprises a first curve 16 and a second curve 17. The second curve 17 is configured to orient the distal end 12 of the conduit 11 towards a straight portion 18 of the conduit 11 and away from the general U-shaped bend 14.

In the illustrated embodiment of FIG. 1, the general U-shaped bend 14 is substantially defined by two radii of curvature. Stated another way, the curvature of the "bottom" of the "U" does not have a constant angle. Instead, each inside corner of the "bottom" of the "U" has its own constant angle of curvature. In the illustrated embodiment of FIG. 1, the radius of curvature, or constant angle of curvature, of each inside corner of the "bottom" of the "U" is roughly equal to the other. As will be discussed in relation to other illustrated embodiments, the general U-shaped bend 14 may be substantially defined by a single radius of curvature or by two or more radii of curvature. The general U-shaped bend 14 may comprise about a 170 degree to about a 190 degree bend, such as about a 180 degree bend.

The conduit 11 may comprise a segment 19 between the general U-shaped bend 14 and the compound curve 15. In the illustrated embodiment of FIG. 1, the segment 19 comprises a substantially straight segment. As will be discussed in relation to other illustrated embodiments, the segment 19 may comprise a substantially curved segment between the general U-shaped bend 14 and the compound curve 15.

The general U-shaped bend 14 and the compound curve 15 may lie in about the same plane.

The compound curve 15 may consist essentially of the first curve 16 and the second curve 17. Additionally, the compound curve 15 may consist of the first curve 16 and the second curve 17.

The first curve 16 may have a radius of curvature that is greater than the radius of curvature of the second curve 17. Stated another way, the first curve 16 may have less curvature than the second curve 17. The first curve 16 may comprise a concave curve relative to a portion of the conduit 11 proximal the first curve 16, such as segment 19. The second curve 17 may comprise a convex curve relative to the first curve 16 and/or relative to the distal end 12.

The distal end 12 may be oriented towards the straight portion 18 at an angle of about 25 degrees to about 50 degrees from the straight portion, including embodiments wherein this angle is about 45 degrees. In the illustrated embodiment of FIG. 1, the distal end 12 is oriented towards the straight portion 18 at an angle of about 30 degrees.

The length of the conduit 11 distal to the general U-shaped bend 14 may be about 5 centimeters to about 13 centimeters, or from about 5 centimeters to about 15 centimeters, including about 10 centimeters. In the illustrated embodiment of FIG. 1, the length of the conduit 11 distal to the general U-shaped bend 14 may be about 5 centimeters.

The distal end 12 of the conduit 11 may lie on the same side of the straight portion 18 as the general U-shaped bend 14 without contacting the straight portion 18, such as in the illustrated embodiment of FIG. 1. Alternatively, the distal end 12 may intersect and/or cross the straight portion 18. In such embodiments, the sidewall of the distal end 12 may contact the sidewall of the straight portion 18.

Figure 19:
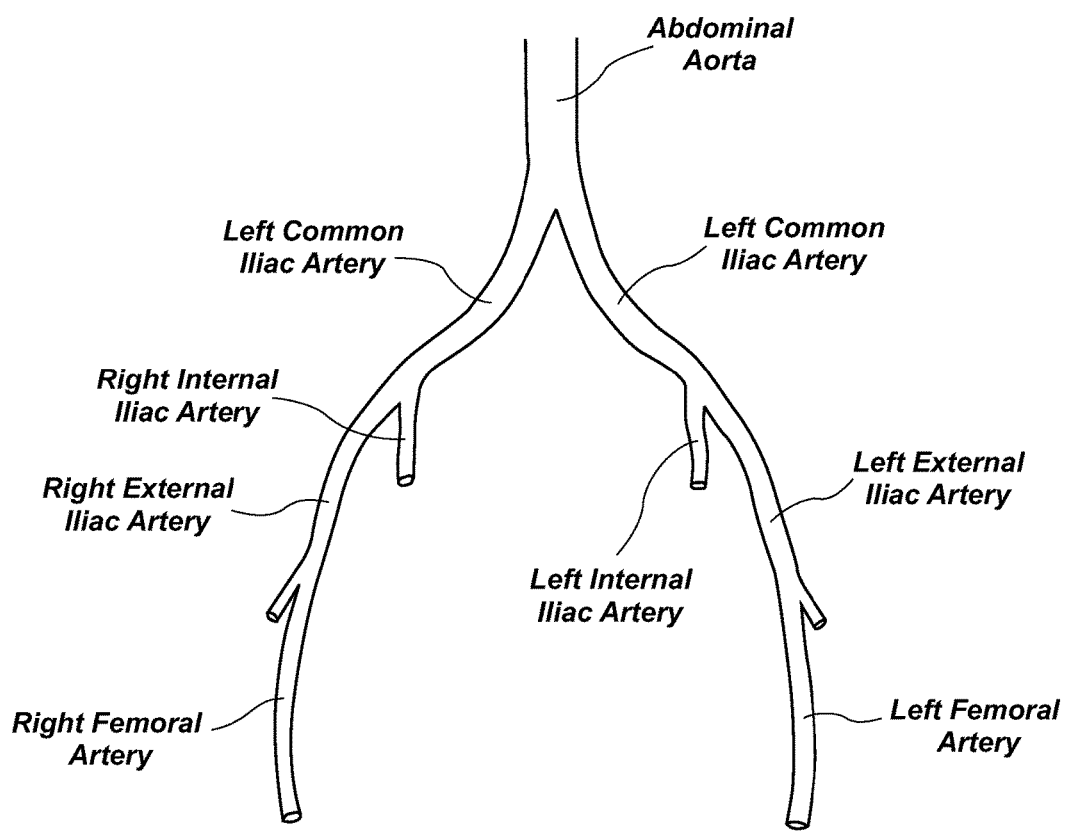
FIG. 19 illustrates an anterior view of the arterial vasculature that supplies blood to the prostate gland of a male patient or the uterus of a female patient.

In some embodiments, the shape of the conduit 11 distal to the general U-shaped bend 14 may be configured to conform generally to the shape of the common iliac artery, either right or left, of an average patient (see FIG. 19). Furthermore, the length of the conduit 11 distal to the general U-shaped bend 14 may be selected so that the distal end 12 is positioned in or near the mouth of the internal iliac artery of an average patient. For example, the distal end 12 may be concentrically positioned in or near the mouth of the internal iliac artery.

For example, the general U-shaped bend 14 and the shape and length of conduit 11 distal to the general U-shaped bend 14 may be configured so as to distort the curvature of the common iliac artery (either right or left) of an average patient to thereby concentrically position the distal end 12 in or near the mouth of the internal iliac artery of the average patient. For example, referring to FIG. 19, the general U-shaped bend 14 may distort outward somewhat the curvature of the right and left common iliac arteries as the general U-shaped bend 14 rests in the arterial fork where the abdominal aorta bifurcates into the right and left common iliac arteries. Likewise, second curve 17 of the conduit 11 may push outward against the interior sidewall of the common iliac artery that is proximal and opposite the mouth of the internal iliac artery (i.e., the branching-off point of the internal iliac artery) to thereby concentrically position the distal end 12 in the mouth of the internal iliac artery.

The conduit 11 may comprise a flexible material, such as a shape memory material, that is capable of deforming and then returning to its original shape. Methods of making the catheter 10 and other catheters disclosed herein are discussed in more detail below.

In some embodiments, the catheter 10 is configured to serve as a delivery catheter for a microcatheter. In some of such embodiments, the conduit 11 may have an outer diameter of about 3.0 French to about 6.0 French, including about 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, and 5.9 French. In some embodiments, the conduit 11 may have an inner diameter of about 1.5 French to about 3.5 French, including about 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, and 3.4 French. The inner diameter of conduit 11 may be sized to conform to, but allow travel of, a microcatheter, such as a standard microcatheter. The microcatheter may have an outer diameter of about 1.5 French to about 3.5 French, including about 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, and 3.4.

FIG. 2 illustrates one embodiment of a catheter 20. FIG. 3 illustrates one embodiment of a catheter 30. FIG. 4 illustrates one embodiment of a catheter 40. It will be appreciated by one of skill in the art having the benefit of this disclosure that analogous portions of the disclosed catheters 10, 20, 30, and 40 may be interchangeable and that disclosure provided in connection with each catheter may be applicable to another.

Catheters 20, 30, and 40 are similar to catheter 10 and differ primarily in the distal length from the general U-shaped bend 14, 24, 34, and 44 to the distal end 12, 22, 32, and 42, respectively. In the illustrated embodiment of FIG. 2, the length of the conduit 21 distal to the general U-shaped bend 24 may be about 7 centimeters. In the illustrated embodiment of FIG. 3, the length of the conduit 31 distal to the general U-shaped bend 34 may be about 10 centimeters. In the illustrated embodiment of FIG. 4, the length of the conduit 41 distal to the general U-shaped bend 44 may be about 13 centimeters.

The difference in the distal length from the general U-shaped bend 14, 24, 34, and 44 may depend primarily upon the difference in length of segment 19, 29, 39, and 49, respectively.

Segments 39 and 49 illustrate segments that are substantially curved. In the illustrated embodiments of FIGS. 3 and 4, the substantially curved segments 39 and 49 have a radius of curvature that is greater than a radius of curvature of the first curve 36 and 46 of the compound curve 35 and 45, respectively. Stated another way, substantially curved segments 39 and 49 have less curvature than first curve 36 and 46, respectively.

Catheters 20, 30, and 40 may also differ from catheter 10 in the angle of distal end 22, 32, and 42 relative to the straight portion 28, 38, and 48, respectively. In the illustrated embodiment of FIG. 2, the distal end 22 is oriented towards the straight portion 28 at an angle of about 40 degrees. In the illustrated embodiment of FIG. 3, the distal end 32 is oriented towards the straight portion 38 at an angle of about 30 degrees. In the illustrated embodiment of FIG. 4, the distal end 42 is oriented towards the straight portion 48 at an angle of about 40 degrees.

It should be understood that a user, such as a surgeon or interventional radiologist, may select between catheters 10, 20, 30, and 40 depending upon the size of the patient. For example, a smaller patient, with corresponding smaller common iliac arteries, may require use of catheter 10 so as to concentrically position the distal end 12 in or near the mouth of the patient's internal iliac artery. In contrast, a taller patient may require the use of catheter 40 so as to concentrically position the distal end 42 in or near the mouth of the patient's internal iliac artery. Average-sized patients may require the use of either catheter 20 or catheter 30.

FIG. 5 illustrates one embodiment of a catheter 50. FIG. 6 illustrates one embodiment of a catheter 60. FIG. 7 illustrates one embodiment of a catheter 70. FIG. 8 illustrates one embodiment of a catheter 80. It will be appreciated by one of skill in the art having the benefit of this disclosure that analogous portions of the disclosed catheters 50, 60, 70, and 80 may be interchangeable with each other and with catheters 10, 20, 30, and 40. The disclosure provided in connection with each catheter may be applicable to another.

Catheter 50 is similar to catheter 10. Catheter 60 is similar to catheter 20. Catheter 70 is similar to catheter 30. Catheter 80 is similar to catheter 40. The primary difference between catheters 50, 60, 70, and 80 and catheters 10, 20, 30, and 40, respectively, is in the "tightness" of the general U-shaped bend 54, 64, 74, and 84. Stated another way, the "bottom" of the "U" has increased angles of curvature in catheters 50, 60, 70, and 80 relative to catheters 10, 20, 30, and 40. As a result, the general U-shaped bend 54 and 84 may each be defined by a single radius of curvature.

The increased "tightness" of the general U-shaped bend 54, 64, 74, and 84 may result in less distortion of the curvature of the right and left common iliac arteries as the general U-shaped bend 54, 64, 74, and 84 rests in the arterial fork where the abdominal aorta bifurcates into the right and left common iliac arteries.

FIGS. 9 through 16 illustrate embodiments of potential variations of the catheters illustrated in FIGS. 1 through 8. FIG. 9 illustrates one embodiment of potential variations in catheter 10 of FIG. 1. In this embodiment, any variation of compound curve 15 and segment 19 that falls within upper limit 11*a* (shown in phantom) and lower limit 11*b* (shown in phantom) and orients distal end 12 towards straight portion 18 is encompassed by the present disclosure and may be used with the methods disclosed herein. These limits are exemplary and are applicable only to this embodiment and are not to be considered limiting of the disclosure, either generally or of the claims hereinafter.

FIG. 10 illustrates one embodiment of potential variations in catheter 20 of FIG. 2. In some embodiments, any variation of compound curve 25 and segment 29 that falls within upper limit 21*a* (shown in phantom) and lower limit 21*b* (shown in phantom) and orients distal end 22 towards straight portion 28 is encompassed by the present disclosure and may be used with the methods disclosed herein. These limits are exemplary and are applicable only to this embodiment and are not to be considered limiting of the disclosure, either generally or of the claims hereinafter.

FIG. 11 illustrates one embodiment of potential variations in catheter 30 of FIG. 3. In some embodiments, any variation of compound curve 35 and segment 39 that falls within upper limit 31*a* (shown in phantom) and lower limit 31*b* (shown in phantom) and orients distal end 32 towards straight portion 38 is encompassed by the present disclosure and may be used with the methods disclosed herein. These limits are exemplary and are applicable only to this embodiment and are not to be considered limiting of the disclosure, either generally or of the claims hereinafter.

FIG. 12 illustrates one embodiment of potential variations in catheter 40 of FIG. 4. In some embodiments, any variation of compound curve 45 and segment 49 that falls within upper limit 41*a* (shown in phantom) and lower limit 41*b* (shown in phantom) and orients distal end 42 towards straight portion 48 is encompassed by the present disclosure and may be used with the methods disclosed herein. These limits are exemplary and are applicable only to this embodiment and are not to be considered limiting of the disclosure, either generally or of the claims hereinafter.

FIG. 13 illustrates one embodiment of potential variations in catheter 50 of FIG. 5. In some embodiments, any variation of compound curve 55 and segment 59 that falls within upper limit 51*a* (shown in phantom) and lower limit 51*b* (shown in phantom) and orients distal end 52 towards straight portion 58 is encompassed by the present disclosure and may be used with the methods disclosed herein. These limits are exemplary and are applicable only to this embodiment and are not to be considered limiting of the disclosure, either generally or of the claims hereinafter.

Figure 14:
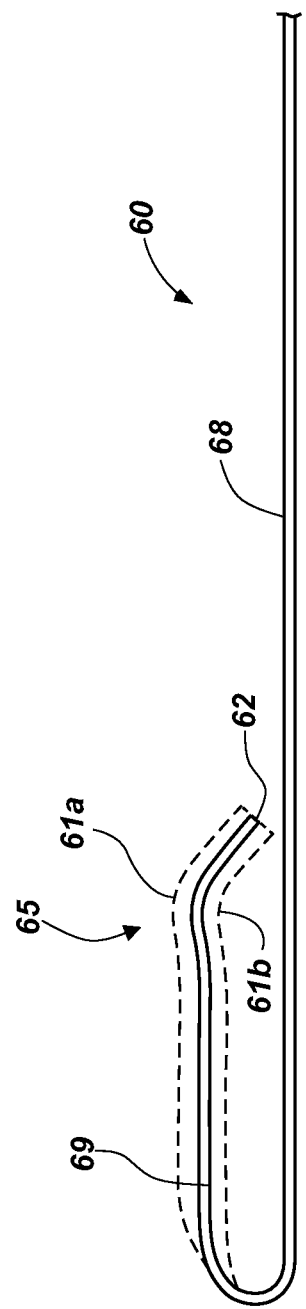
FIG. 14 illustrates one embodiment of potential variations in the embodiment illustrated in FIG. 6.

FIG. 14 illustrates one embodiment of potential variations in catheter 60 of FIG. 6. In some embodiments, any variation of compound curve 65 and segment 69 that falls within upper limit 61*a* (shown in phantom) and lower limit 61*b* (shown in phantom) and orients distal end 62 towards straight portion 68 is encompassed by the present disclosure and may be used with the methods disclosed herein.

Figure 15:
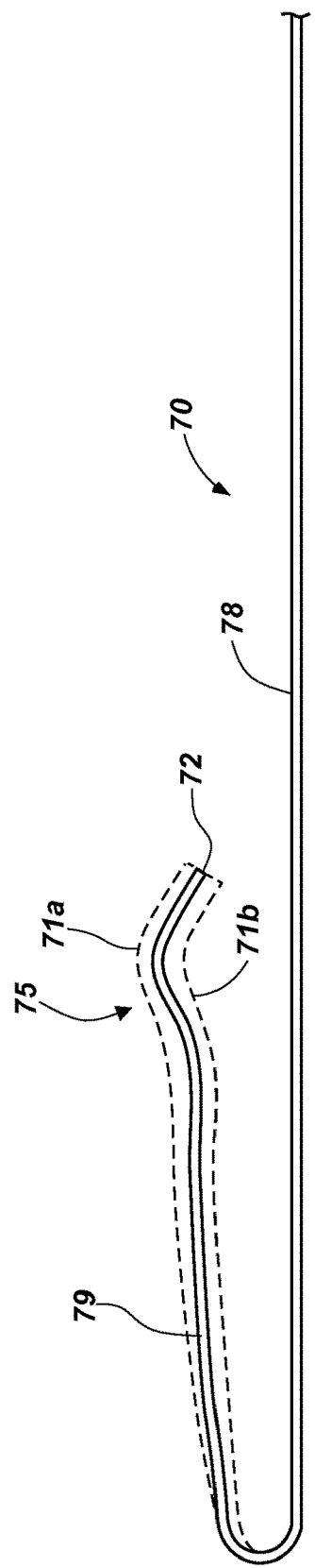
FIG. 15 illustrates one embodiment of potential variations in the embodiment illustrated in FIG. 7.

FIG. 15 illustrates one embodiment of potential variations in catheter 70 of FIG. 7. In some embodiments, any variation of compound curve 75 and segment 79 that falls within upper limit 71*a* (shown in phantom) and lower limit 71*b* (shown in phantom) and orients distal end 72 towards straight portion 78 is encompassed by the present disclosure and may be used with the methods disclosed herein. These limits are exemplary and are applicable only to this embodiment and are not to be considered limiting of the disclosure, either generally or of the claims hereinafter.

Figure 16:
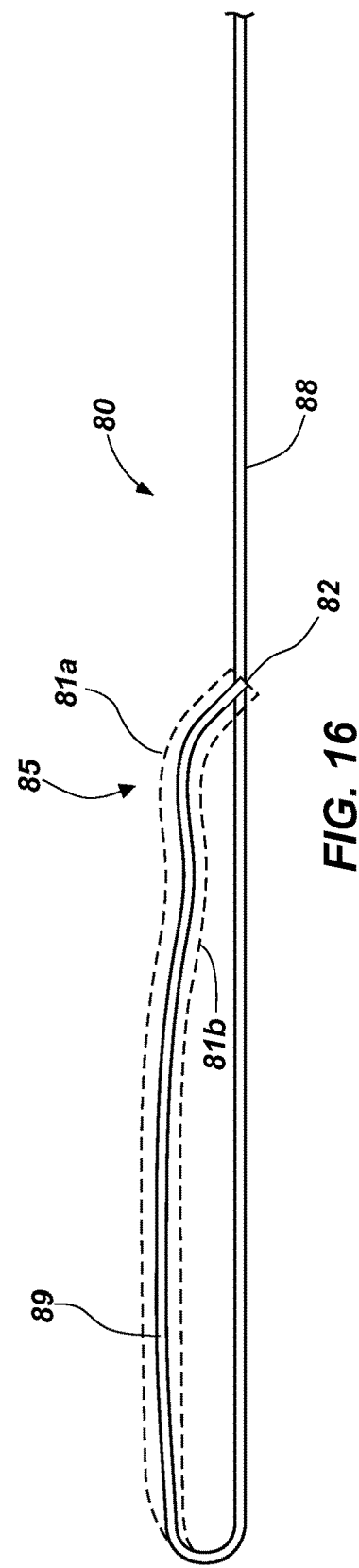
FIG. 16 illustrates one embodiment of potential variations in the embodiment illustrated in FIG. 8.

FIG. 16 illustrates one embodiment of potential variations in catheter 80 of FIG. 8. In some embodiments, any variation of compound curve 85 and segment 89 that falls within upper limit 81*a* (shown in phantom) and lower limit 81*b* (shown in phantom) and orients distal end 82 towards straight portion 88 is encompassed by the present disclosure and may be used with the methods disclosed herein. Regarding catheter 80, it should be understood that, while the distal end 82 may lie on or extend beyond the straight portion 88, it is still considered to be oriented towards the straight portion 88, as the region proximal the distal end 82 is oriented towards the straight portion 88. These limits are exemplary and are applicable only to this embodiment and are not to be considered limiting of the disclosure, either generally or of the claims hereinafter.

Figure 17:
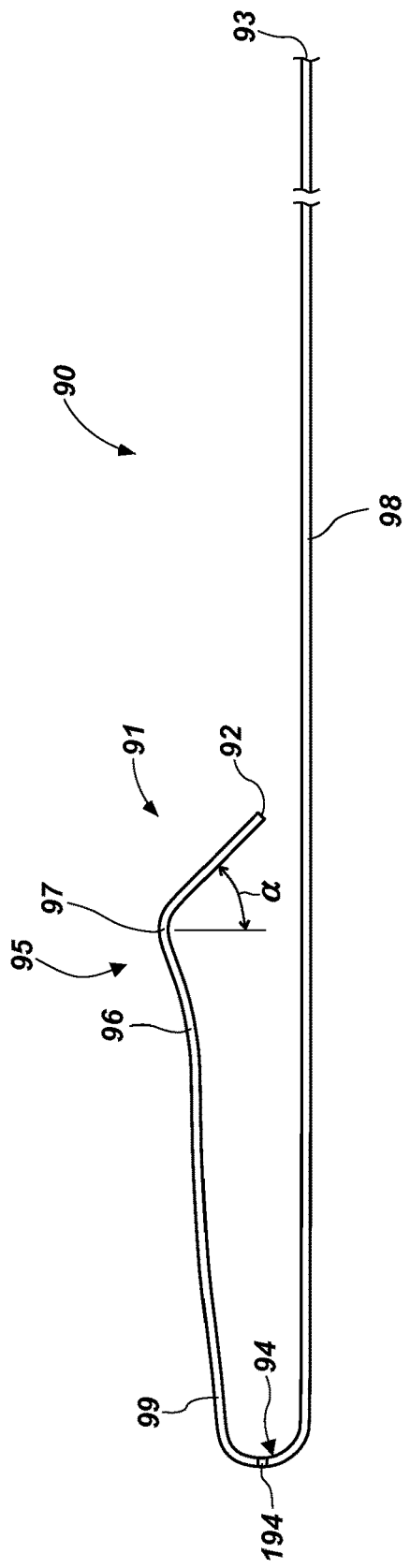
FIG. 17 is a side view of another embodiment of a catheter.

FIG. 17 illustrates one embodiment of a catheter 90. As with the other embodiments disclosed herein, various portions or features of the catheter 90 may resemble portions or features of the other catheters disclosed herein, such as catheter 10 of FIG. 1. It will be appreciated by one of skill in the art, having the benefit of this disclosure, that all the illustrated embodiments have analogous features and components. Accordingly, like or analogous features are designated with like reference numerals, with the leading digits incremented. Relevant disclosure set forth in connection with one embodiment regarding similarly identified features thus may not be repeated in connection with the other embodiments. Moreover, specific features of each catheter may not be shown or identified by a reference numeral in the all the drawings or specifically discussed in the written description. However, such features may clearly be the same, or substantially the same, as features depicted in other embodiments and/or described with respect to such embodiments. Accordingly, the relevant descriptions of such features apply equally to the features of the other embodiments. Any suitable combination of the features, and variations of the same, described with respect to any single embodiment may be applied to any other embodiment. This pattern of disclosure applies equally to all the embodiments depicted herein.

Catheter 90 comprises a conduit 91. The conduit 91 may comprise a single lumen. The conduit 91 comprises a distal end 92 configured for vascular insertion and a proximal end 93. The conduit 91 also comprises a general U-shaped bend 94 near the distal end 92. The conduit 91 further comprises a compound curve 95 between the distal end 92 and the general U-shaped bend 94. The compound curve 95 comprises a first curve 96 and a second curve 97. The second curve 97 is configured orient the distal end 92 of the conduit 91 toward a straight portion 98 of the conduit 91 and away from the general U-shaped bend 94. The conduit 91 may also comprise a segment 99 between the general U-shaped bend 94 and the compound curve 95. In some embodiments, the segment 99 may be generally straight.

As compared to the catheter 20 of FIG. 2, the catheter 90 of FIG. 17 may extend a greater distance from the second curve 97 to the distal end 92. In some embodiments the length of the conduit 91 from the general U-shaped bend 94 to the second curve 97 may be between 4 and 6 times the length of the conduit 91 between the second curve 97 and the distal end 92, including embodiments where it is 5 times the length.

The length of the conduit 91 distal to the general U-shaped bend 94 may be from about 5 centimeters to about 15 centimeters, including from about 7 centimeters to about 14 centimeters. In some embodiments, this length may be about 5 centimeters, about 7 centimeters, about 10 centimeters, about 14 centimeters, or about 15 centimeters.

As indicated by angle α of FIG. 17, the portion of the conduit 91 distal of the second curve 97 may extend at an angle relative to the straight portion 98 of the conduit 91. In the illustrated embodiment, the reference line defining the left bound of the angle α is perpendicular to the straight portion 18, meaning that angle α is complimentary to the angle formed between the portion of the conduit 91 distal the second curve 97 and the straight portion 98. In other words, the sum of these angles will be 90 degrees. Angle α may be from about 30 degrees to about 60 degrees, or about 40 degrees to about 50 degrees, meaning the complimentary angle may be between the same ranges. In some embodiments, angle α is about 45 degrees, as is its complimentary angle.

The catheter 90 may further comprise a marker band 194 disposed on the conduit 91. The marker band 194 may comprise a material with a higher radiopacity than the conduit 91 material. Thus, the marker band 194 may facilitate viewing of the conduit 91 through radio imaging. In some embodiments, the marker band 194 may be disposed at the general U-shaped bend 94, including embodiments wherein the marker band 194 is disposed in the middle of the general U-shaped bend 94.

The catheters disclosed herein have been described in relation to their unflexed or undistorted state, such as when in a sterile package prior to use in a medical procedure. It should be understood that when being inserted into the vasculature of a patient, the shape of the catheter may be distorted by rigid guidewires and/or the vasculature itself. For example, referencing FIG. 1 and FIG. 19, the general U-shaped bend 14 and compound curve 15 of catheter 10 may be substantially straightened by a rigid guidewire while catheter 10 is introduced into the right femoral artery of a patient. Catheter 10 may be kept in a substantially straight condition as catheter 10 is advanced through the right external iliac artery and right common iliac artery. Distal end 12 may be advanced somewhat further into the abdominal aorta. The rigid guidewire may then be partially retracted to allow at least second curve 17 to regain its curved shape. Catheter 10 may be rotated so that distal end 12 extends into the left common iliac artery. The rigid guidewire and catheter 10 may then be advanced further into the left common iliac artery. The rigid guidewire may be fully withdrawn from catheter 10 once distal end 12 is positioned in or near the mouth of the left internal iliac artery.

Methods of using a catheter are disclosed herein. In one embodiment, the methods comprise inserting a catheter comprising a conduit into a femoral artery on one side of a patient. The methods may further comprise directing the catheter through an external iliac artery and a common iliac artery on that side of the patient. The methods further comprise directing the catheter through a common iliac artery on the other side of the patient. The methods may comprise resting a generally U-shaped bend in the conduit of the catheter in a bifurcation of both of the common iliac arteries from the abdominal aorta artery. The methods may also comprise placing a distal end of the conduit in or near a mouth of the internal iliac artery on the other side of the patient, wherein the conduit distal to the general U-shaped bend is configured to conform generally to a shape of a right or left common iliac artery of an average patient.

In some embodiments, the general U-shaped bend and the conduit distal to the general U-shaped bend are configured to distort the shape of the common iliac artery on the other side of the patient so as to concentrically position the distal end of the conduit in or near the mouth of the internal iliac artery on the other side of the patient.

The methods may further comprise inserting a microcatheter into a lumen of the conduit of the catheter and advancing the microcatheter into arteries that branch off of the internal iliac artery in or near which the distal end of the catheter is positioned. The methods may further comprise injecting embolic materials, such as microspheres or microparticles, via the microcatheter into the arteries to occlude blood flow in the arteries. For example, the arteries may be prostatic or uterine arteries.

The methods may further comprise advancing a microguidewire, via the lumen of the microcatheter, into arteries that branch from the internal iliac artery and then using the microguidewire to direct placement of the microcatheter in a particular artery. The microguidewire may then be removed and contrast agent injected via the microcatheter to determine whether the artery feeds the targeted organ or tissue, such as the prostate or uterus.

The methods may be used to treat any disease or disorder associated with increased growth of a tissue or organ supplied with blood by the right and/or left internal iliac artery of a patient. For example, the methods may be used to treat Benign Prostate Hyperplasia (BPH), prostate cancer, uterine fibroids, or adenomyosis.

Figure 18:
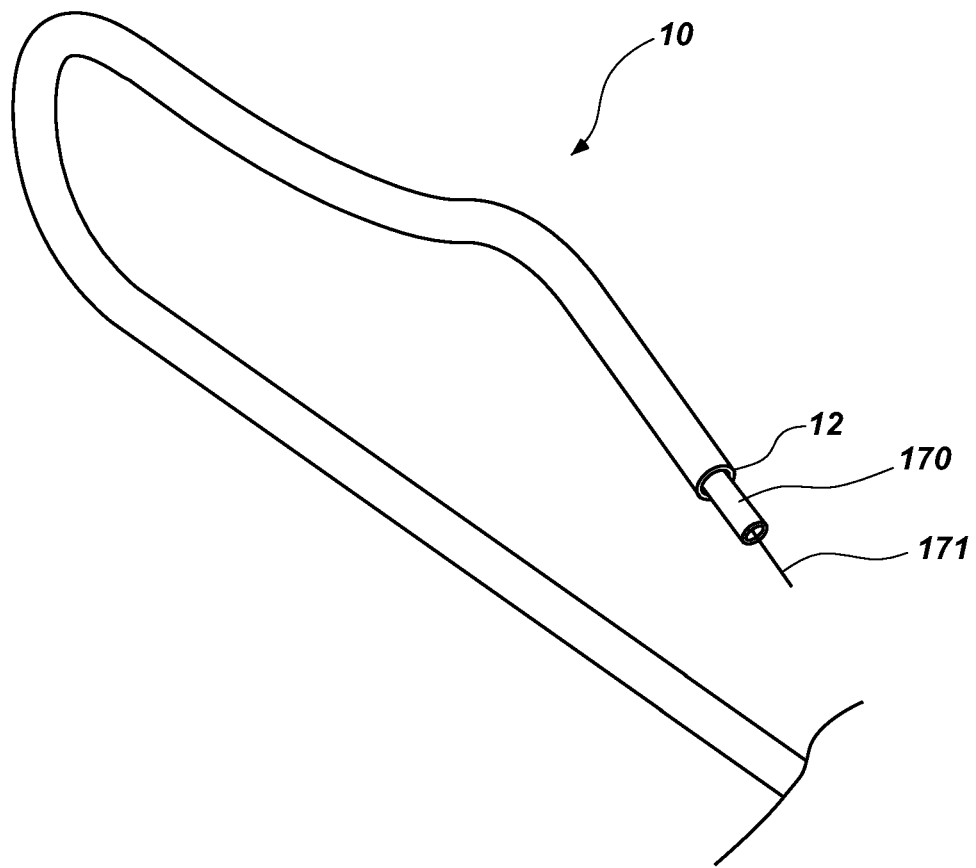
FIG. 18 illustrates a perspective view of the distal end of the embodiment illustrated in FIG. 1 with a microcatheter and microguidewire extending beyond the distal end of the catheter.

In some embodiments, the methods may use any one of catheters 10, 20, 30, 40, 50, 60, 70, and/or 80. For example, FIG. 18 illustrates a perspective view of catheter 10 of FIG. 1 with a microcatheter 170 and microguidewire 171 extending beyond the distal end 12.

Methods of manufacturing a catheter are also disclosed herein. The methods may comprise extruding a polymeric tube. A mandrel may be inserted into a lumen of the tube, wherein the mandrel comprises a general U-shaped bend near the distal end of the mandrel. The mandrel may further comprise a compound curve between the general U-shaped bend and the distal end of the mandrel. The compound curve may comprise a first curve and a second curve, wherein the second curve is configured to orient the distal end of the mandrel towards a straight portion of the mandrel and away from the general U-shaped bend of the mandrel. The tube may then be placed in a hot air bath to set the tube in the shape of the mandrel. The mandrel may then be removed from the tube.

The methods of manufacturing may also comprise extruding a hollow tip and fusing the tip to the tube. The mandrel may then be inserted into the tip as well as the tube.

The tube may comprise at least one layer of wire braiding. The tube may comprise a flexible material, such as a shape memory material, that is capable of deforming and then returning to its original shape.

While specific embodiments of catheters and methods of using and making catheters have been illustrated and/or described, it is to be understood that the disclosure provided is not limited to the precise configuration and components disclosed. Various modifications, changes, and variations apparent to those of skill in the art having the benefit of this disclosure may be made in the arrangement, operation, and details of the devices, methods, and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not as a limitation of the scope of the present disclosure in any way. It will be apparent to those having skill in the art, and having the benefit of this disclosure, that changes may be made to the details of the above-described embodiments without departing from the underlying principles of the disclosure herein.

The invention claimed is:

1. A method for vascular insertion of a catheter, the method comprising:
   providing the catheter, the catheter comprising:
      a conduit comprising a distal end configured for vascular insertion and a proximal end;
      wherein the proximal end comprises a straight portion when the conduit is unconstrained;
      wherein the conduit comprises a general U-shaped bend near the distal end of the conduit;
      wherein the conduit further comprises a compound curve disposed between the general U-shaped bend and the distal end;
      wherein a length of the conduit from the straight portion to the compound curve is not tapered;
      wherein the compound curve comprises a first curve and a second curve, the first curve disposed between the U-shaped bend and the second curve;
      wherein the first curve comprises a concave curve such that a distal segment of the first curve extends away from the straight portion of the proximal end;
      wherein the second curve comprises a convex curve such that a distal segment of the second curve extends toward the straight portion of the proximal end;
      wherein the distal end of the conduit is oriented towards the straight portion of the proximal end and away from the general U-shaped bend;
      wherein a length of the conduit distal to the general U-shaped bend is about 5 centimeters to about 15 centimeters;
      wherein a length of the conduit proximal to the general U-shaped bend is sized to extend from a femoral artery to a bifurcation of both common iliac arteries from an aorta artery; and
      wherein the conduit further comprises a lumen with an inside diameter;
   disposing the catheter within both common iliac arteries such that the U-shaped bend is disposed at the bifurcation, the distal segment of the first curve extends away from an internal iliac artery, and the distal segment of the second curve extends toward a mouth of the internal iliac artery.

2. The method of claim 1, wherein the general U-shaped bend comprises about a 170 degree to about a 190 degree bend.

3. The method of claim 1, further comprising a substantially curved section between the general U-shaped bend and the compound curve and wherein the substantially curved segment has a radius of curvature that is greater than a radius of curvature of the first curve of the compound curve.

4. The method of claim 1, wherein the first curve has a radius of curvature that is greater than a radius of curvature of the second curve.

5. The method of claim 1, wherein the convex curve is convex relative to the distal end of the conduit.

6. The method of claim 1, wherein the distal end of the conduit is oriented towards the straight portion of the conduit at an angle of about 25 degrees to about 50 degrees from the straight portion.

7. The method of claim 1, wherein the distal end of the conduit lies on the same side of the straight portion as the general U-shaped bend.

8. The method of claim 1, wherein the distal end of the conduit intersects the straight portion of the conduit, wherein a sidewall of the distal end of the conduit contacts a sidewall of the straight portion of the conduit.

9. The method of claim 1, wherein a shape of the conduit distal to the general U-shaped bend is configured to conform generally to a shape of a common iliac artery of an average human patient.

10. The method of claim 1, wherein the conduit has an outer diameter of about 3.0 French to about 6.0 French.

11. The method of claim 1, wherein the conduit inside diameter is about 1.5 French to about 3.5 French.

12. A method for vascular insertion of a catheter, the method comprising:
   providing the catheter, the catheter comprising:
      a conduit comprising a distal end configured for vascular insertion and a proximal end;
      wherein the proximal end comprises a straight portion when the conduit is unconstrained;
      wherein the conduit comprises a general U-shaped bend near the distal end of the conduit;
      wherein the conduit further comprises a compound curve disposed between the general U-shaped bend and the distal end;

wherein a length of the conduit from the straight portion to the compound curve is not tapered;

wherein the compound curve comprises a first curve and a second curve, the first curve disposed between the U-shaped bend and the second curve;

wherein the first curve comprises a concave curve such that a distal segment of the first curve extends away from the straight portion of the proximal end;

wherein the second curve comprises a convex curve such that a distal segment of the second curve extends toward the straight portion of the proximal end;

wherein the distal end of the conduit is oriented towards the straight portion of the proximal end and away from the general U-shaped bend; and wherein the conduit further comprises a lumen with an inside diameter;

disposing the catheter such that the general U-shaped bend rests in a bifurcation of both common iliac arteries from an aorta artery such that the straight portion is disposed within a common iliac artery on one side of a patient and the length of the conduit from-the U-shaped bend to the distal end positions the distal end adjacent an internal iliac artery on the other side of the patient.

13. The method of claim 12, wherein the second curve pushes outward against an interior sidewall of the common iliac artery that is proximal and opposite a mouth of the internal iliac artery to position the distal end in the mouth of the internal iliac artery.

* * * * *